United States Patent [19]

DiGiacomo et al.

[11] 4,390,690
[45] * Jun. 28, 1983

[54] LAYERED ORGANOPHOSPHOROUS INORGANIC POLYMERS CONTAINING OXYGEN BONDED TO CARBON

[75] Inventors: Peter M. DiGiacomo, Mission Viejo; Martin B. Dines, Santa Ana, both of Calif.

[73] Assignee: Occidental Research Corp., Irvine, Calif.

[*] Notice: The portion of the term of this patent subsequent to Nov. 4, 1997, has been disclaimed.

[21] Appl. No.: 273,027

[22] Filed: Jun. 12, 1981

Related U.S. Application Data

[63] Continuation of Ser. No. 60,249, Jul. 24, 1979, abandoned, which is a continuation-in-part of Ser. No. 945,971, Sep. 26, 1978, Pat. No. 4,232,146.

[51] Int. Cl.$^3$ .................. C08G 79/04; C08G 79/00
[52] U.S. Cl. .................. 528/395; 260/429.3; 260/429.5; 260/429 R; 260/429 J; 260/429.7; 260/435 R; 528/271; 528/398
[58] Field of Search .............. 528/395, 271, 398; 260/429 R, 429 J, 429.3, 429.5, 429.7, 435

[56] References Cited

U.S. PATENT DOCUMENTS

| | | | |
|---|---|---|---|
| 2,512,063 | 6/1950 | Kreidl et al. | 528/395 |
| 3,231,347 | 1/1966 | Revukas | 44/69 |
| 3,415,781 | 12/1968 | Block et al. | 528/395 |
| 3,445,492 | 1/1972 | Washburn et al. | 260/429.7 |
| 3,491,133 | 1/1970 | Revukas | 260/429.7 |
| 3,615,807 | 10/1971 | Yates | 106/288 B |
| 3,634,479 | 5/1969 | Ridenour | 260/429.7 |
| 3,663,460 | 5/1972 | Block et al. | 260/33.6 R |
| 3,681,265 | 8/1972 | Krueger | 528/271 |

FOREIGN PATENT DOCUMENTS 2614356 10/1977 Fed. Rep. of Germany .
539293 9/1941 United Kingdom .
1406419 9/1975 United Kingdom .
170968 6/1965 U.S.S.R. .

OTHER PUBLICATIONS

Journal of Inorganic & Nuclear Chemistry, vol. 40, pp. 1113-1117, Jun. 1978, (Constantino et al.).
Chem. Abstract 83, 70750g (1975).
Chem. Abstract 85, 13433y (1976).
Chem. Abstract 86, 155758c (1977).
Chem. Abstract 58, 1487b (1963).
Chem. Abstract 55, 11161c (1961).
Dub, "Organometallic Compounds," Springer-Verlog, Berlin VIII, pp. 187-191, (1962).
Doak, et al., "Organometallic Compounds of Arsenic, Antimony and Bismuth," Wiley, Intersc., N.Y., pp. 46-49 (1970).

Primary Examiner—Wilbert J. Briggs, Sr.
Attorney, Agent, or Firm—Christie, Parker & Hale

[57] ABSTRACT

A process for the production of phosphorus-containing organo-substituted solid inorganic polymers containing oxygen bonded to carbon comprising reacting in a liquid medium (e.g. water) at least one tetravalent metal ion and at least one organophosphorus acid of the formula;

$$[(HO)_2OP]_nR \text{ or } [(HO)_2OPO]_nR$$

wherein n is 1 or 2 and R is an organo group covalently coupled to phosphorus, and which also contains oxygen coupled to carbon but not to phosphorus, and wherein when n is 2, R contains at least two carbon atoms and is directly or indirectly coupled to the phosphorus atoms through different carbon atoms whereby the two phosphorus atoms are separated by at least two carbon atoms.

27 Claims, 8 Drawing Figures

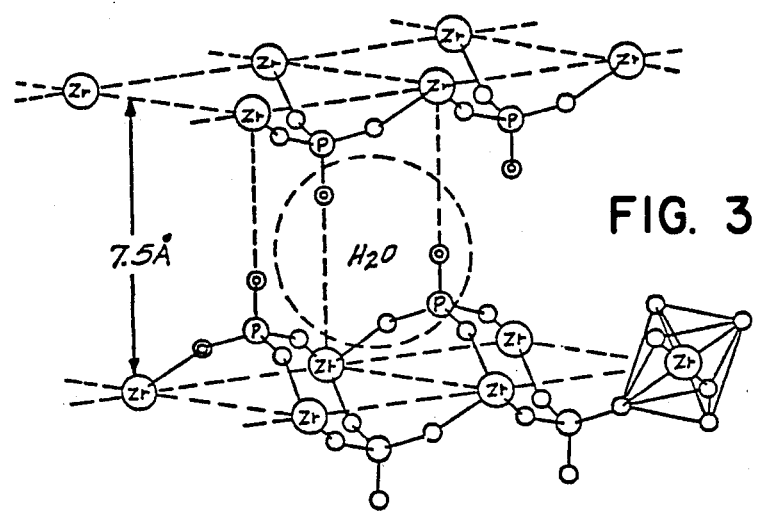
FIG. 3
FIG. 5
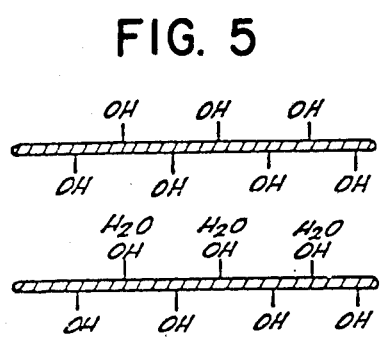
FIG. 4
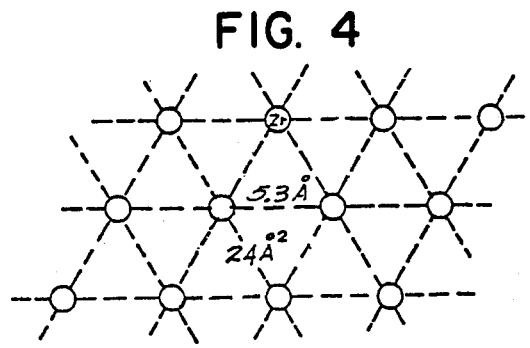
FIG. 6
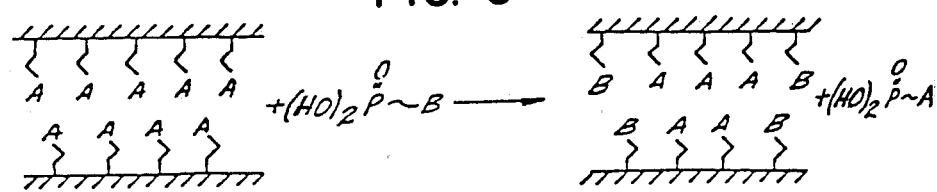

4,390,690

LAYERED ORGANOPHOSPHOROUS INORGANIC POLYMERS CONTAINING OXYGEN BONDED TO CARBON

CROSS-REFERENCE TO RELATED APPLICATIONS

This application is a continuation of application Ser. No. 60,249, filed July 24, 1979, now abandoned, which is a continuation-in-part of application Ser. No. 945,971, filed Sept. 26, 1978, now U.S. Pat. No. 4,232,146, issued Nov. 4, 1980, and is related to the following copending applications: Ser. No. 952,228 filed Oct. 17, 1978, now U.S. Pat. No. 4,235,990 issued Nov. 25, 1980; Ser. No. 966,197 filed Dec. 4, 1978, now U.S. Pat. No. 4,235,991 issued Nov. 25, 1980 Ser. No. 7,275 filed Jan. 29, 1979, Ser. No. 43,810 filed May 30, 1979 and titled Process for Preparing Layered Organophosphorus Inorganic Polymers; Ser. Nos. 54,107 and 54,097 filed July 2, 1979 and titled, respectively, Layered Cyano End Terminated Organophosphorus Inorganic Polymers and Layered organophosphorus Inorganic Polymers Containing Mercapto or Thio Groups; and four applications filed concurrently herewith on July 24, 1979, and titled Layered Organophosphorus Inorganic Polymers Containing Cyclic Groups Ser. No. 60,077; Layered Organoarsenous Inorganic Polymers Ser. No. 60,078; Layered Organophosphorus Inorganic Polymers Containing Acyclic Groups Ser. No. 60,079; and Layered Organophosphorus Inorganic Polymers Containing Mixed Functional Groups Ser. No. 60,250. The entire disclosure of each of these applications is hereby incorporated herein by this reference.

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids are responsive regions of chemical and physical action. In many practical chemical and physical phenomena such as absorption, corrosion, inhibition, heterogeneous catalysis, lubrication, ion exchange activity, adhesion and wetting and electrochemistry activity occurs as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in their active sites which arises from the nature of their surface structure. Furthermore, much of the active sites are usually buried within the surface, and as a result of these two factors, elevated temperature and low conversions are typically encountered. Exceptions in which homogeneous catalysts are employed have been the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Efforts at heterogenizing catalysts have been discussed by Bailar, "Heterogenizing Homogeneous Catalysts," Catalysis Reviews—Sci. & Eng. 10(1) 17-35 (1974) and Hertley and Vezey, "Supported Transition Metal Complexes as Catalysts," Advances in Organometallic Chemistry 15, 189-235 (1977). The entire disclosure of which is incorporated herein.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "interclalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, this potential surface will be greater than the actual surface by a factor of the number of lamella composing the crystal. This value is typically on the order of $10^2$–$10^4$. Although edge surface is practically insignificant compared to basal surface, it is critical in the rate of intercalation, since the inclusion process always occurs via the edges. This is because bonding within the sheets is strong, and therefore, basal penetration of the sheets in an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process on deintercalation the guests undergo only minor perturbation.

In order for a more active process to occur during intercalation, such as selective complexation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ion or van der Waals forces of intercalated guests were operating.

One of the few layered compounds which have potential available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be promising inorganic cation exchanger for alkali, ammonium and actinide ions, Alberti, "Accounts of Chem. Research", 11, 163 (1978), incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. S. Yamaka described the reaction of this solid with ethylene oxide, which does not simply incorporate between the layers as do the other organics, but rather was found to irreversibly react with the acidic hydroxyls to form a covalently bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound inorganic alkanol groups. This conversion, while of interest, has limited if any improvement over the hydroxyls already available on zirconium phosphate.

A very recently reported effort in the field is Alberti, et al., "J. Inorg. Nucl. Chem.", 50, 1113 (1978) which is incorporated herein by reference. A method similar to that of this invention for the preparation of zirconium bis(benzenephosphonate), zirconium bis(hydroxymethanephosphonate) monohydrate, and zirconium bis(monoethylphosphate) is described, with descriptions of the properties for these products.

Following the Alberti publication, a paper by Maya appeared in "Inorg. Nucl. Chem. Letters", 15, 207 (1979), describing the preparation, properties and utility as solid phases in reversed phase liquid chromatography for the compounds $Zr(O_3POC_4H_9)_2 \cdot H_2O$, $Zr(O_3POC_{12}H_{25})_2$ and $Zr(O_3POC_{14}H_{21})_2$. All of the compositions that are described herein can be useful in gas phase, liquid phase, gas liquid, reversed phase, and bulk and thin layer chromatography. The compounds can also be useful as hosts and carriers for organic molecules and especially biologically active organic molecules (e.g. methoprene).

SUMMARY OF THE INVENTION

This invention deals with layered organophosphorus inorganic polymers containing oxygen bonded to carbon. Preferably, the organic moiety of these polymers have an empirical formula, R—O—R' or

wherein R is an organo group containing a carbon bonded to the oxygen, which can be cyclic (including heterocyclic) or acyclic, which can be partially or wholly halosubstituted and which can contain one or more reactive substituents (e.g., nitrate, sulfonate, amino, etc.), and wherein R' is selected from hydroxide, hydrogen or an organo group containing carbon bonded to the oxygen which can be the same or different from R and which can be cyclic (including heterocyclic or acyclic, which can be partially or wholly halogen substituted (e.g., F, Cl, Br, I) and which can contain one or more reactive substituents (e.g., nitrate, sulphonate, amino, etc.

More preferred, R is a hydrocarbon substituent (which can be partially or wholly halosubstituted) and R' is a hydrocarbon substituent, hydrogen, hydroxyl O—R' wherein R" is a hydrocarbon substituent, which can be the same or different as R and R'. Typically, the organic moiety is an alcohol, ether, peroxide, peroxy acid, ketone, aldehyde, carboxylic acid ester or amide.

According to the present invention there is provided solid inorganic polymers having organo groups covalently bonded to phosphorus atoms and in which the phosphorus atoms are, in turn, covalently bonded by oxygen linkage to tetravalent metal atoms and, when formed in a layered crystalline state, provide the organo groups on all of the apparent and interlamellar surfaces.

The process of preparation comprises a liquid medium reaction in which at least one organophosphorus acid compound of the formula:

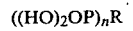

wherein n is 1 or 2 and R is an organo group covalently coupled to the phosphorus atom, and wherein when n is 2, R contains at least two carbon atoms and is directly or indirectly coupled to phosphorus atoms through different carbon atoms whereby the two phosphorus atoms are separated by at least two carbon atoms, is reacted with at least one tetravalent metal ion preferably selected from the group consisting of zirconium, cerium, thorium, uranium, lead, hafnium and titanium. The molar ratio of phosphorous to the tetravalent metal is 2 to 1. Reaction preferably occurs in the presence of an excess of the organophosphorus acid compound and the metal ion is provided as a compound soluble in the liquid medium.

Where only one specie of an organophosphorus acid compound is provided as the reactant with the tetravalent metal compound, the end product will have the empirical formula $M(O_3PR)_2$. Phosphoric and/or phosphorous acid can also be present as reactive dilutants to form part of the solid inorganic polymeric structure which is the product of the reaction.

The products formed are layered crystalline to amorphous in nature. For all products, the R groups may be directly useful or serve as intermediates for the addition or substitution of other functional groups. When the product is crystalline and n is 2, cross-linking between the interlamellar layers occurs.

The normal liquid medium is water. However, organic solvents, particularly ethanol, may be employed where water will interfere with the desired reaction. Preferably, the solvent is the solvent in which the organophosphorus acid compound is prepared. Where the organophosphorus acid compound has a sufficiently low melting point, it can serve as the liquid media.

The metathesis reaction occurs at temperatures up to the boiling point of the liquid medium at the pressures involved, typically from ambient to about 150° C. more preferably from ambient to about 100° C. While formation of the solid inorganic polymer is almost instantaneous, the degree of crystallinity of the product can be increased by refluxing the reaction products for times from about 5 to 15 hours. Crystallinity is also improved by employing a sequestering agent for the tetravalent metal ion.

THE DRAWINGS

Figure 1:
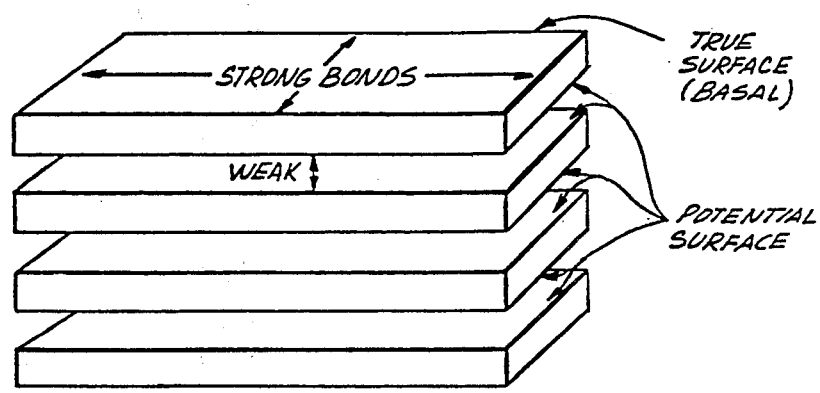
FIG. 1 illustrates a layered microcrystal. Each lamellar slab is formed of strong covalent bonds and has a thickness of about 10 atoms.
Figure 2:
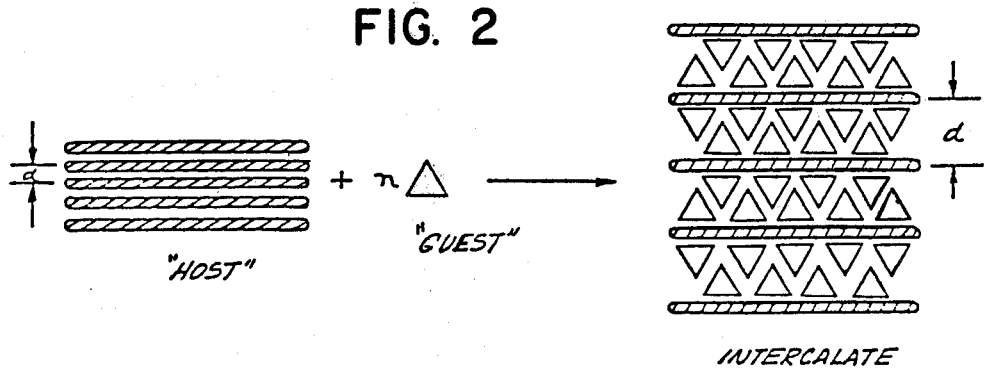
FIG. 2 illustrates intercalation where the interlayer distance is shown as "d."

FIG. 3 illustrates the accepted structure for zirconium phosphate and spacing between layers. The dashed lines between zirconium (Zr) atoms is to establish the plane between them. In the drawing P=phosphorus, O=oxygen and water of hydration is shown.

FIG. 4 illustrates a projection of zirconium plane showing accepted spacing between Zr atoms and the available linkage area.

FIG. 5 is a symbolized depiction of spaced zirconium phosphate layers showing covalently bonded hydroxyl groups and water of hydration.

FIG. 6 illustrates an exchange reaction between anchored groups "A" and groups to be substituted for "B", and 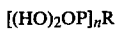 represents the portion of the organo group linking the terminal group "A" or "B" to the crystals or the organophosphorus acid compound reactant.

Figure 7:
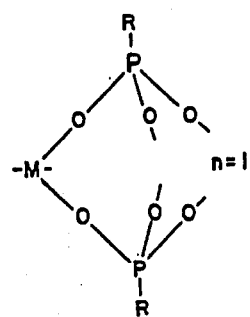

FIG. 7 shows the basic structural unit of the inorganic polymer formed by the process of the invention where n is 1 and where P=phosphorus atom, O=oxygen atom, M=tetravalent metal atom and R is the organo group.

Figure 8:
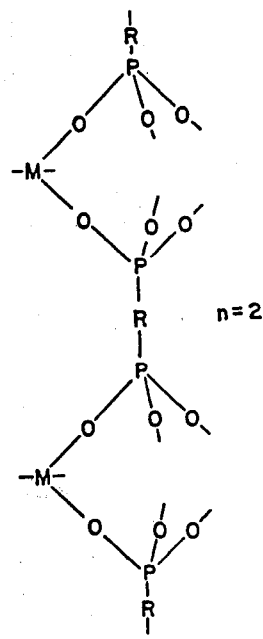

FIG. 8 shows the basic structural unit of the inorganic polymer formed by the Process of the invention where n is 2 and where P=phosphorus atom, O=oxygen atom, M=tetravalent metal atom and R is the organo group.

DETAILED DESCRIPTION

According to the present invention there is provided solid inorganic polymers in layered crystalline to amorphous state by the liquid phase metathesis reaction of at least one organophosphorus acid compound having the formula:

$$[(HO)_2OP]_nR$$

wherein n is 1 or 2 and R is an organo group covalently coupled to the phosphorus atom, with at least one tetravalent metal ion selected from the group consisting of zirconium, thorium, cerium, uranium, lead, hafnium and titanium to form a solid inorganic polymer precipitate in which phosphorus is linked to the metal by oxygen and the organo group is covalently bonded to the phosphorus atom. Where, in the organophosphorus compound, n is 2, the end product occurs in the bis configuration. In this configuration, R must contain two or more carbon atoms, preferably from two to about twenty carbon atoms, such that at least two carbon atoms separate the phosphorus atoms. In this bis configuration no single carbon atom is bound directly or indirectly to more than one $[PO(OH)_2]$ group. When n is 1, and as depicted in FIG. 7, the organo groups will be pendant from phosphorus atoms. When n is 2, and as depicted in FIG. 8, cross-linking will occur between interlamellar surfaces of the crystalline end product. Typically, the tetravalent metal ion is provided as a soluble salt MX wherein M is as defined above and X is the anion(s) of the salt. The typical anions include halides, $HSO_4^{-1}$, $SO_4^{-2}$, $O_2C-CH_3^{-1}$, $NO_3^{-1}$, $O^{-2}$ and the like.

The majority of the polymeric reaction products formed are found to be layered crystalline or semi-crystalline in nature and, as such, provided layered structures similar to zirconium phosphates. The remainder are amorphous polymers possessing a large quantity of available pendant groups similar to silica gel.

By the term "organophosphorus acid compound", as used herein, there is meant a compound of the formula:

$$[(HO)_2OP]_nR$$

wherein n is 1 or 2, R is any group which will replace a hyroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is presently preferred.

When, in the organophosphorus compound, n is 2, the end product occurs in the bis configuration. In this configuration, R must contain three or more carbon atoms, preferably from two to about twenty-six carbon atoms, such that at least two carbon atoms separate the phosphorus atoms. In this bis configuration, no single carbon atom is bound directly or indirectly to more than one $[PO(OH)_2]$ group. Thus the groups which link to the metal have the basic structural formula:

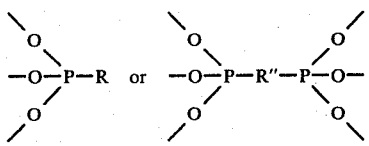

wherein R" is a bis group containing at least two carbon atoms bonded directly or indirectly to phosphorus, such that no phosphorus atoms are bonded directly or indirectly to the same carbon atom. The basic structures of the inorganic polymer forms are shown in FIGS. 7 and 8.

When coupling is through carbon, the organo phosphorus acid compound is an organo phosphonic acid and the product a phosphonate. When coupling is through oxygen-carbon, the organophosphorus acid compound is an organo-phosphoric monoester acid and the product a phosphate.

The general reaction for phosphonic acids alone is shown in equation (1) below and for monoesters of phosphoric acid alone by equation (2).

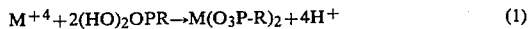

$$M^{+4} + 2(HO)_2OPR \rightarrow M(O_3P\text{-}R)_2 + 4H^+ \qquad (1)$$

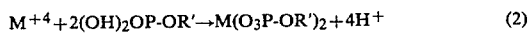

$$M^{+4} + 2(OH)_2OP\text{-}OR' \rightarrow M(O_3P\text{-}OR')_2 + 4H^+ \qquad (2)$$

wherein R' is the remainder of the organo group.

The product contains phosphorus to metal in a molar ratio of about 2 to 1, and the empirical formula for the product would show all organo groups bound to phosphorus.

While nowise limiting, the R groups attachable to phosphorus may be saturated and unsaturated, substituted and unsubstituted and include, among others, alkylene, alkyloxy, alkyne, aryl, haloalykl, alkylaryl, aryloxy, mercaptoalkyl, aminoalkyl, carboxyalkyl, morpholinoalkyl, sulfoalkyl, phenoxyalkyl, beta-diketo alkyl, cyanoalkyl, cyanoalkoxy, heterocyclics and the like.

In general, the organo group should occupy no more than about 25 Å² for proper spacing. This limitation is imposed by the basic crystal structure of zirconium phosphate. Referring to FIG. 4, a spacing of 5.3 Å is shown between zirconium atoms in the zirconium plane of a crystal for a total area of about 24 Å² is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 Å², adjacent groups may be somewhat larger than 24 Å² and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE 1

| Moiety | Minimum Area (Å²) | Moiety | Minimum Area (Å²) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphine | 50(approx.) |
| Morpholinomethyl | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the organophosphorus acid compounds are water soluble, an organic solvent such as ethanol may be employed, where water interferes with the reaction. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the organophosphorus acid compound may serve as a solvent. Typically, the liquid medium is the liquid medium in which the organophosphorus acid is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reaction and provide an inorganic polymer diluted in respect to the organo group in proportion to the amount of phosphorous or phosphoric acid employed.

Reaction is virtually instantaneous at all temperatures leading to precipitation of layered crystalline, semi-crystalline or amorphous inorganic polymer solid.

The amorphous phase appears as a gel similar to silica gel. The gel can be crystallized by extended reflux in the reaction medium, usually from about 5 to about 15 hours. The semi-crystalline product is characterized by a rather broad X-ray powder diffraction pattern.

The presence of sequestering agents for the metal ion slows down the reaction and also leads to more highly crystalline products. For instance, a semi-crystalline solid has been prepared by the aqueous phase reaction of zirconiumoxychloride and excess 2-carboxyethyl phosphonic acid, followed by 15 hours of reflux. A highly crystalline modification was prepared under identical conditions except that hydrogen fluoride was added to the reaction mixture. A slow purge of N₂ over the surface of the reaction solution slowly removed the fluoride from the system. Fluoride is a very strong complexing agent for zirconium ions. The slow removal of fluoride results in slow release of the metal ion for reaction with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium and the rate of formation of this product is slow and the product polymer quite crystalline.

As compared to zirconium phosphate forming crystals of 1–5 microns, the crystals of 100 to greater than 1000 micron in size have been prepared in accordance with the invention.

A property critical for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525° C., indicating remarkable stability. Decomposition of zirconium 2-carboxyethylphosphonate begins between 300° and 400° C. The decomposition process inflection point, approximate mid-point, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis affirmed covalent bonding to phosphorous. This is because normal intercalative interactions are reversed within 10° to 100° C. above the boiling point of the guest.

The process disclosed herein permits a wide variety of inorganic polymers to be formed having the characteristic of the organo group protected by the inorganic polymer structure and, with subsequent exchange or substitution reactions, the formation of other inorganic polymers. Polymers formed may be block, random and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphite phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, ths band was shifted to 2440 cm$^{-1}$ and broadened.

Another route is to exchange one pendant group for another. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction such as

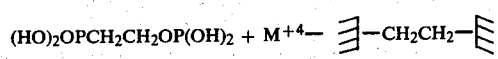

$(HO)_2OPCH_2CH_2OP(OH)_2 + M^{+4} \longrightarrow$ where as in FIG. 6, ⊥⊥⊥⊥⊥⊥⊥ represents the interlamellar layer to which the alkyl group is anchored. As with all organo groups, for the bis configuration at least two carbon atoms are present, preferably from two to twenty atoms, and the phosphorus atoms are linked directly or indirectly to different carbon atoms. Since size of the linking group will control and fix interlamellar spacing, there is provided effective laminar sieves of fixed spacing for application analogous to that of molecular sieves.

Ion exchange activity as been established with pendant carboxylic acid groups. Prepared zirconium 2-carboxyethyl phosphonate was established to have an interlayer distance of 12.8 Å. When intercalated to form its n-hexylammonium salt interlayer distance increased to 27.2 Å. When sodium was taken up, layer spacing increased to 14.2 Å. X-ray and infrared data indicated the highly crystalline inorganic polymer to behave as expected for carboxylic acid with behavior analogous to ion exchange resins except that both external and internal surfaces were functional establishing them as super surface ion exchange resins. Moreover, since the inorganic polymers can be prepared as microcrystalline powders, diffusion distances are short.

As summarized in Table II, nitrile and mercapto anchored groups show the ability to take up silver and copper ions at room temperature ion catalytic activity.

TABLE II

| Anchored Group | Metal Ion | Loading | mMole Metal / mMole Zr |
|---|---|---|---|
| —O~CN | 0.1 M Ag$^+$ | | 0.20 |
| ~SH | 0.1 M Ag$^+$ | | 1.00 |
| —O~CN | 0.1 M Cu$^{++}$ | | 0.10 |
| —O~CN | 0.1 M Cu$^{++}$ | 0.5 M HOAc | 0.10 |
| | | 0.5 M NaOAc | |

~ = groups formed of carbon and hydrogen.
OAc = acetate radical.

The alternate to catalytic utility is to attach the metals to the organophosphorus acid prior to reaction with the soluble tetravalent metal compound.

The high surface area of the crystalline products also make them utile for sorption of impurities from aqueous and non-aqueous media.

Another utility is as an additive to the polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals, substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from suppliers. The products formed are insoluble in normal solvents and do not sublime. However, the combined weight of yield data, spectroscopy, elemental analyses and powder diffraction results confirm the compositions reported with good reliability.

EXAMPLE I

Preparation of: Th(O$_3$PCH$_2$OH)$_2$

To the reaction flash was added 0.552 g of

which was dissolved in about 10 ml of water. The solution was then mixed with a solution containing 1.353 g of Th(NO$_3$)$_4$·4H$_2$O dissolved in about 20 ml of water. About ¾ ml of a 38 percent solution of hydrogen chloride was also added.

Upon the mixing of the two solutions a precipitate slowly appeared over a time of about ten minutes. The reaction mixture was then heated overnight. Following heating the reaction mixture was cooled and filtered to separate the formed solid precipitate from the liquid. The recovered solid was washed with successive washes of water and acetone. The recovered solid was then dried for about one hour at 100° C. The dried Th(O$_3$PCH$_2$OH)$_2$ solid weighed 1.126 g.

Elemental analysis of the recovered product provided the following results: C 2.30, H 2.26. An X-ray powder diffraction pattern showed the compound to be crystalline, having an interlayer spacing of 9.51 Å.

EXAMPLE II

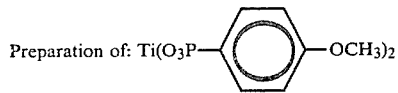

In a reaction flash was added 0.979 g of

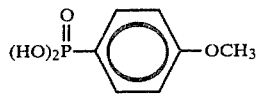

dissolved in ethanol. To the flask was also added 1.168 g of a 30 percent by weight aqueous solution of TiOCl$_2$.

Upon mixing a white precipitate formed. The reaction mixture was refluxed for about 8 hours. The precipitate formed was light yellow in color. Following the refluxing period the reaction mixture was allowed to stand at room temperature over a weekend.

The reaction mixture was then filtered to recover the solid

The solid recovered was washed with successive washes of water, methanol, and acetone. The solid was then air dried at room temperature, then dried in an oven at 100° C. After drying the solid, the solid weighed about 0.902 g and was a light yellow color.

Elemental analysis of the recovered product provided the following results: C=40.12; H=3.55; P=14.6; T=11.2. An X-ray powder diffraction pattern showed the compound to be crystalline, having an interlayer spacing of 18.4 Å.

This composition and that of Example I can be useful as chromatographic stationary phases or supports.

EXAMPLE III

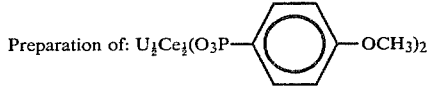

In a reaction vessel was mixed about 3 g of ceric sulfate (H$_4$Ce(SO$_4$)$_4$) about 85 percent and water in an amount sufficient to substantially dissolve the ceric sulfate. The insolubles formed were separated by filtration in two separate filtering steps. The second filtration being performed upon the formation of additional insolubles in the solution. Ceric sulfate decomposes rapidly and for such reasoning generally cannot be quantitatively measured. The above manner of forming a ceric sulfate solution is generally utilized to provide a substantially stable aqueous solution of the solid.

To the clear yellow resulting solution of H$_4$Ce(SO$_4$)$_4$ was added an ethanol solution containing 0.400 g of

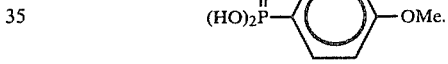

The H$_4$Ce(SO$_4$)$_4$ was present in excess over the

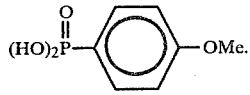

A precipitate formed upon mixing. The reaction mixture was refluxed a few minutes with stirring as the precipitate formed. The precipitate was allowed to settle and the supernatant liquid containing the excess ceric salt was decanted.

A separate solution was prepared by dissolving 0.404 g of UCl$_4$ in ethanol. This solution was mixed with an ethanol solution of a stoichiometric amount, 0.400 g of

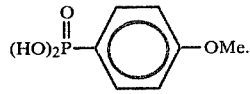

A light green precipitate formed immediately upon mixing. The precipitate was allowed to settle at room temperature.

The two precipitates formed by the above reactions were mixed together. Water was added to the two mixed precipitates and the mixture was refluxed for about eight hours. Following refluxing the reaction mixture was allowed to cool at room temperature over the weekend.

The reaction mixture was filtered to separate the precipitate formed. The solid

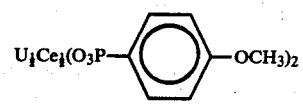

was washed with water followed by an acetone wash and air dried. Following drying, the recovered solid weighed 0.648 g and was a light green colored powder.

This example illustrates the making of a polymetallic layered compound, such compositions are useful as chromatographic stationary supports (see the publication of L. Maya cited herein).

EXAMPLE IV

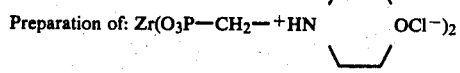

To a 100 ml round-bottom flask was charged 5.64 g of morpholinemethylphosphonic acid (14.1 g of 40% aqueous solution), 5.01 g $ZrOCl_2.8H_2O$ and about 8 ml of water. The solution was stirred at room temperature overnight. No precipitate formed. The entire reaction mixture was added to 110 ml of ethanol and a fine white solid precipitated. About half of this slurry was charged to a 100 ml reaction flask and refluxed gently over the weekend. The product was collected by filtration, washed with ethanol and dried under vacuum. The solid product weighed 6.5 g.

This composition can be useful as an anion exchange agent or as a metal ion complexing agent when in the free-base form or as a chromatographic stationary phase.

EXAMPLE V

Esterification of zirconium-3-carboxypropyl phosphonate with n-butanol

To 100 ml three-necked flask was charged 5.0 g of zirconium-3-carboxypropylphosphonate, 40 g n-butanol and 10 g $H_2O$. To this was added 3 ml of HCl as catalyst. The slurry was refluxed and water removed azeotropically. After about one day, 40 ml of fresh butanol was added and azeotropic distillation continued for about a week. The product was isolated by filtration and washed with acetone and ethyl ether. The dry product weighed 5.44 g. The infrared spectrum clearly shows the conversion from the carboxylic acid to the ester. This material can be used as a host or carrier for biologically active organic molecules (e.g., methoprene).

EXAMPLE VI

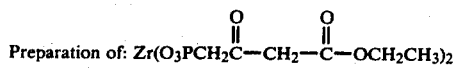

To a reaction flask was added 1.646 g of ethyl 4-chloro-aceto-acetate in 20 ml of acetone. Added to the flask was 1.80 g of NaI dissolved in 12 ml of acetone. The resulting slurry was stirred. A few grains of sodium thiosulfate was added to complex with the iodine released.

A yellow solution formed upon mixing the two solutions in which formed a white solid, NaCl. The solid phase formed took up most of the solution volume. Produced was

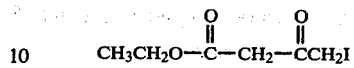

in an amount of 3.164 g.

In a separate reaction flask was added 1.50 g of the iodo ketone product produced above. To the reaction flask was then added 2.00 g of triethyl phosphite. Upon mixing, a bubbling occurred and the reaction mixture changed from dark red to an iodine color. The mixture was heated to 50° C. for about 25 minutes. An orange gel appeared which, after separation, weighed 4.731 g which was

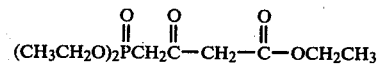

Upon NMR analysis there was shown to be 19 hydrogens. Upon gas chromatographic analysis, two peaks were predominant of equal intensity.

The $(CH_3CH_2O)_2PCH_2C$—$CH_2$—$C$—$OCH_2CH_3$ was reacted with trimethyl silyl iodide to produce

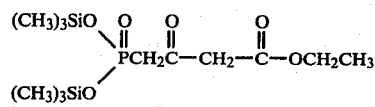

Into a three-necked flask was placed 1.164 g of $Zr(OC_3H_7)_4$ dissolved in 10.0 ml of carbon tetrachloride and 2.300 g of the silated product produced above dissolved in 10 ml carbon tetrachloride. A precipitate appeared almost immediately. The reaction mixture appeared to thicken. An additional 20 ml of carbon-tetrachloride for a total of 40 ml $CCl_4$. The reaction mixture was allowed to react over the weekend.

The reaction mixture was filtered to collect the precipitate that had formed. The recovered precipitate was washed with $CCl_4$ followed by ether. Repeated ether washes were performed until the solid was a cream white color. The recovered solid weighed 1.343 g.

An infrared analysis evidenced a C=O stretching was present.

Other metal$^{+4}$ ions which are analogous to $Zr^{+4}$ in the process to make phosphate and phosphonate analogs, are metals with approximately the same ionic radius as $Zr^{+4}$ (0.8 Å), for example,

| | | | | | | | | |
|---|---|---|---|---|---|---|---|---|
| $Zr^{+4}$ | 0.08Å | $Te^{+4}$ | 0.81 | $Pr^{+4}$ | 0.94 | $Mn^{+4}$ | 0.5 |
| $W^{+4}$ | 0.66 | $Sn^{+4}$ | 0.71 | $Pb^{+4}$ | 0.92 | $Ir^{+4}$ | 0.66 |
| $U^{+4}$ | 0.89 | $Si^{+4}$ | 0.41 | $Os^{+4}$ | 0.67 | $Hf^{+4}$ | 0.81 |
| $Ti^{+4}$ | 0.68 | $Ru^{+4}$ | 0.65 | $Nb^{+4}$ | 0.67 | $Ge^{+4}$ | 0.53 |
| $Th^{+4}$ | 0.95 | $Pu^{+4}$ | 0.86 | $Mo^{+4}$ | 0.68 | $Ce^{+4}$ | 1.01 |

The thio analogs of the phosphonates and phosphates can also be made by this process. The larger, more readily redoxable elements can lead to semiconducting, photoactive supports. All of the above noted solid, layered compounds can be useful as a chromatographic solid phase, adsorbants ion-exchange and hosts or carriers for controlled release of active substances.

In the preparation of anchorable Layered Compounds, a general approach to zirconium phosphate and the other zirconium compositions described herein and in the applications incorporated herein involve the following concepts:

(1) Tetrahedral anions with 3-metal coordinating groups and one interlayer group desirable

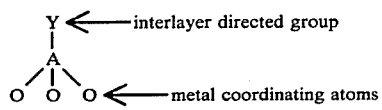

(2) Charge on anion should be $-1$, $-2$, $-3$ (charge on metal ion therefore should be $+2$, $+4$, $+6$ for $M[O_3AY]_2$ stoichiometry needed for sandwiching and bridging configuration)

(i) for $-1$ charge, conjugate acid of anion is

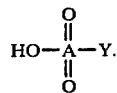

"A" can be S (or Se, Cr, Mo, W, etc., ($+6$ forming elements)

(ii) for $-2$ charge, conjugate acid of anion

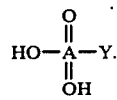

"A" can be P, As, Sb, V, Nb, Ta, etc., ($+5$ forming elements)

(iii) for $-3$ charge, conjugate acid of anion is

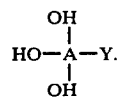

"A" can be Si, Ge, Ti, Zr, Sn, Pb ($+4$ forming elements).

Some exemplary salts which meet these criteria are listed below.

$M[O_3A-Y]_2$: Examples of compounds of structure which can form layered host structures analogous to zirconium phosphate and the phosphorous or arsenic containing compounds of the applications incorporated herein:

(1) $[O_3A-Y]^{-1}$: A=S, for example, Y=NH$_2$ (conjugate acid is sulfamic acid) M+ = $Cu^{+2}$, $Zn^{+2}$, $Fe^{+2}$, alkaline earths

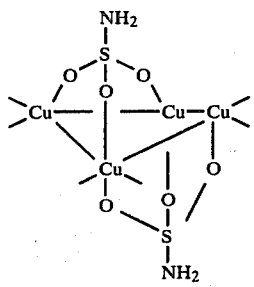

(2) $[O_3A-Y]^{-2}$: Zirconium phosphate prototypes (A=P, As, Sb, etc.)

$[O_3A-Y]^{-3}$: A=Si, for example, Y=OCH$_2$CN, M=Mo$^{+6}$

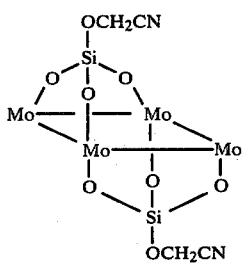

In all cases, metal ion is in octahedral sphere (could be trigonal prism)

Although the structure of these solid phases is polymeric in nature, it is convention in solid inorganic nomenclature to refer to them by their monomeric units.

What is claimed is:

1. A process for the production of phosphorus containing organo substituted inorganic polymers containing oxygen bonded to carbon which comprises reacting in a liquid medium:

(a) at least one organophosphorus acid of the formula

[(HO)$_2$OP]$_n$R or [(HO)$_2$OPO]$_n$R wherein n is 1 or 2 and R is an organo group covalently coupled to phosphorus and which also contains oxygen coupled to carbon but not to phosphorus and wherein when n is 2, R contains at least two carbon atoms and is directly or indirectly coupled to the phosphorus atoms through different carbon atoms whereby the two phosphorus atoms are separated by at least two carbon atoms, (b) with at least one tetravalent metal ion, to precipitate from the liquid medium, a solid inorganic polymer in which the molar ratio of phosphorus to tetravalent metal is about 2 to 1 and in which the organo group is covalently bonded to phosphorus and phosphorus is linked to the tetravalent metal through oxygen.

2. The process of claim 1 in which the liquid medium is a liquid medium in which the organo phosphorus acid compound is formed.

3. The process of claim 1 in which the liquid medium is water.

4. The process of claim 1 in which the metal of said tetravalent metal ion is selected from zirconium, cerium, thorium, uranium, titanium, lead and combinations of two or more said metals.

5. The product of the process of claim 1.

6. The product of the process of claim 4.
7. The process of claim 4 wherein said organophosphorus acid is a phosphoric acid.
8. The process of claim 4 wherein said organophosphorus acid is an organophosphorous acid.
9. The process of claim 4 wherein said acid is selected from hydroxymethyl-phosphonic acid, 4-methoxy phenyl phosphonic, N-morpholinomethylphosphonic acid and 3-carboxypropyl phosphonic acid.
10. The product of the process of claim 9.
11. Process for esterification of a carboxy-end terminated phosphorus-tetravalent metal inorganic solid comprising reacting said solid with an alcohol and an acid catalyst.
12. Process of claim 1 where R is an oxidizable or reducible oxygen-containing function.
13. Process of claim 12, wherein said function is of the quinone-hydroquinone type.
14. The product of the process of claim 13.
15. The use of the product of claim 13 as a redox-catalyst.
16. The use of claim 13 wherein hydrogen peroxide is produced using said redox-catalyst.
17. A process for the production of phosphorus-containing, organo-substituted, layered inorganic polymers containing oxygen bonded to carbon which comprises reacting in a liquid medium:
(a) at least one organophosphorus acid of the formula

[(HO)$_2$OP]$_n$R or [(HO)$_2$OPO]$_n$R wherein n is 1 or 2 and R is an organo group covalently coupled to phosphorus and which also contains oxygen coupled to carbon but not to phosphorus and wherein when n is 2, R contains at least two carbon atoms and is directly or indirectly coupled to the phosphorus atoms through different carbon atoms whereby the two phosphorus atoms are separated by at least two carbon atoms,
(b) with at least one tetravalent metal ion, to precipitate from the liquid medium, a solid comprising layered inorganic polymers in which the molar ratio of phosphorus to tetravelent metal is about 2 to 1 and in which the organo group is covalently bonded to phosphorus and phosphorus is linked to the tetravlanet metal through oxygen.
18. A process for the production of phosphorus-containing, organo-substituted inorganic polymers containing oxygen bonded to carbon which comprises reacting in a liquid medium:
(a) at least one organophosphorus acid of the formula

[(HO)$_2$OP]$_n$R or [(HO)$_2$OPO]$_n$R wherein n is 1 or 2 and R is an organo group covalently coupled to phosphorus and which also contains oxygen coupled to carbon but not to phosphorus and wherein when n is 2, R contains at least two carbon atoms and is directly or indirectly coupled to the phosphorus atoms through different carbon atoms whereby the two phosphorus atoms are separated by at least two carbon atoms,
(b) with at least one tetravalent metal ion, to precipitate from the liquid medium, a solid comprising spaced apart sheets of inorganic polymers in which the molar ratio of phosphorus to tetravalent metal is about 2 to 1 and in which the organo group is covalently bonded to phosphorus and phosphorus is linked to the tetravalent metal through oxygen.
19. A process for the production of phosphorus containing organo-substituted inorganic polymers including a carbon-oxygen-carbon bond, the process comprising reacting in a liquid medium:
(a) at least one organophosphorus acid of the formula:

[(HO)$_2$OP]$_n$R or [(HO)$_2$OPO]$_n$R wherein n is 1 or 2 and R comprises an organo group covalently coupled to phosphorus and which includes a carbon-oxygen-carbon bond, wherein when n is 2, R contains at least two carbon atoms and is directly or indirectly coupled to the phosphorus atoms through different carbon atoms whereby the two phosphorus atoms are separated by at least two carbon atoms; and
(b) at least one tetravalent metal ion to precipitate from the liquid medium a solid inorganic polymer in which the molar ratio of phosphorus to tetravalent metal is about 2 to 1 and in which the organo group is covalently bonded to phosphorus and phosphorus is linked to the tetravalent metal through oxygen.
20. A phosphorus-containing organo-substituted layered inorganic polymer including structural units having the empirical formula:

M(O$_3$PO$_n$R)$_2$ or M(O$_3$PO$_n$R"PO$_3$)

wherein n is 0 or 1, R comprises an organo group covalently coupled to phosphorus and which also contains oxygen coupled to carbon but not phosphorus, R" comprises an organo group containing at least two carbon atoms bonded directly or indirectly to the phosphorus through different carbon atoms whereby the phosphorus atoms are separated by at least two carbon atoms and containing oxygen coupled to carbon and not to phosphorus, M comprises a tetravalent metal structurally linked to phosphorus through oxygen and wherein the molar ratio of phosphorus to tetravalent metal is about 2 to 1.
21. A phosphorus-containing organo-substituted layered inorganic polymer including structural units having the empirical formula:

M(O$_3$PO$_n$R)$_2$ or M(O$_3$PO$_n$R"PO$_3$)

wherein n is 0 or 1, R comprises an organo group covalently coupled to phosphorus and which also includes a carbon-oxygen-carbon bond, R" comprises an organo group containing at least two carbon atoms bonded directly or indirectly to the phosphorus through different carbon atoms whereby the phosphorus atoms are separated by at least two carbon atoms and including a carbon-oxygen-carbon bond, M comprises a tetravalent metal structurally linked to phosphorus through oxygen and wherein the molar ratio of phosphorus to tetravalent metal is about 2 to 1.
22. A phosphorus-containing organo-substituted layered inorganic polymer as recited in claim 20 or 21 wherein the tetravalent metal is selected from the group consisting of zirconium, thorium, cerium, uranium, lead, hafnium and titanium.

23. A phosphorus-containing organo-substituted layered inorganic polymer including structural units comprising the formula:

Th(O₃PCH₂OH)₂

24. A phosphorus-containing organo-substituted layered inorganic polymer including structural units comprising the formula:

25. A phosphorus-containing organo-substituted layered inorganic polymer including structural units comprising the formula:

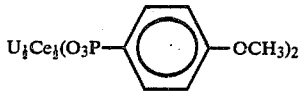

26. A phosphorus-containing organo-substituted layered inorganic polymer including structural units comprising the formula:

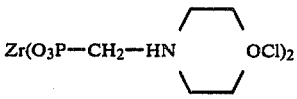

27. A phosphorus-containing organo-substituted layered inorganic polymer including structural units comprising the formula:

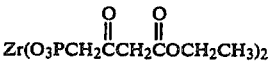

* * * * *